United States Patent [19]

Husbands et al.

[11] Patent Number: 4,826,844

[45] Date of Patent: May 2, 1989

[54] SUBSTITUTED 1-(ARALKYL-PIPERAZINOALKYL) CYCLOALKANOLS

[75] Inventors: G. E. M. Husbands, Berwyn; Gary P. Stack, Merion, both of Pa.

[73] Assignee: American Home Products Corporation, New York, N.Y.

[21] Appl. No.: 102,695

[22] Filed: Sep. 30, 1987

[51] Int. Cl.$^4$ .................. A61K 31/505; C07D 403/04
[52] U.S. Cl. .................................. 514/252; 514/183; 514/218; 514/253; 514/255; 540/470; 540/575; 544/295; 544/357; 544/377; 544/394; 544/397
[58] Field of Search ............... 544/295, 357, 377, 394, 544/397; 514/252, 253, 255, 183, 218; 540/470, 575

[56] References Cited

U.S. PATENT DOCUMENTS 2,971,955  2/1961  Zaugg et al. .................. 544/391
4,535,186  8/1985  Husbands et al. .................. 564/336

OTHER PUBLICATIONS

Zaugg et al., "J.A.C.S.", vol. 80, No. 11, 1958, pp. 2773–2774.

Primary Examiner—Glennon H. Hollrah
Assistant Examiner—James H. Turnipseed
Attorney, Agent, or Firm—Richard K. Jackson

[57] ABSTRACT

Compounds of the formula:

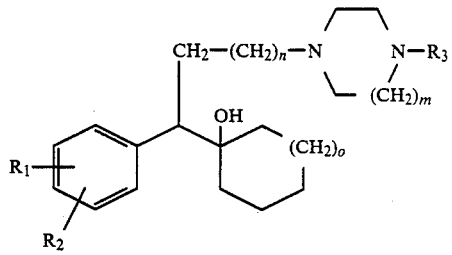

in which m is one of the integers 1, 2 or 3; n is one of the integers 0, 1 or 2; o is one of the integers 0, 1 or 2; $R_1$ and $R_2$ are, independently, hydrogen, hydroxyl, alkyl, alkoxy, alkanoyloxy, trifluoromethyl, halo, or, when taken together, 3,4-methylenedioxy; $R_3$ is alkyl,

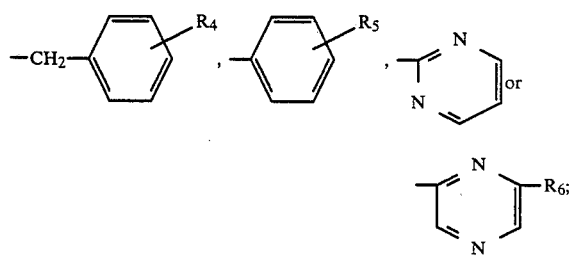

where $R_4$ and $R_5$ are, independently, hydrogen, hydroxyl, alkyl, alkoxy, alkanoyloxy, halo or trifluoromethyl; and $R_6$ is hydrogen or halo; or a pharmaceutically acceptable salt thereof.

36 Claims, No Drawings

SUBSTITUTED 1-(ARALKYL-PIPERAZINOALKYL) CYCLOALKANOLS

DESCRIPTION OF THE INVENTION

In accordance with this invention there is provided a group of N-substituted phenylalkylpiperazines which are useful in the treatment of psychiatric disorders classified as psychosis, depression and anxiety. The compounds of this invention present the structural formula:

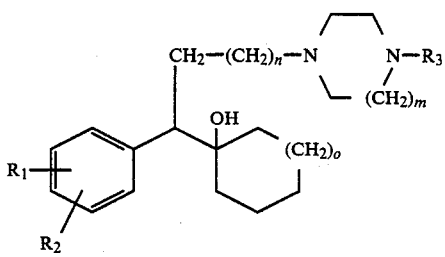

in which
  m is one of the integers 1, 2 or 2;
  n is one of the integers 0, 1 or 2;
  o is one of the integers 0, 1 or 2;
  $R_1$ and $R_2$ are, independently, hydrogen, hydroxyl, alkyl of 1 to 6 carbon atoms, alkoxy of 1 to 6 carbon atoms, alkanoyloxy of 2 to 7 carbon atoms, trifluoromethyl, halo, or, when taken together, 3,4-methylenedioxy;
  $R_3$ is alkyl of 1 to 3 carbon atoms,

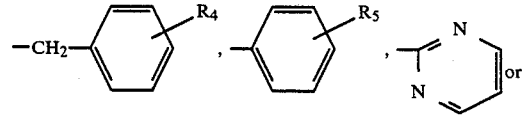 or 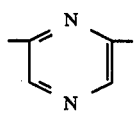

where $R_4$ and $R_5$ are, independently, hydrogen, hydroxyl, alkyl of 1 to 6 carbon atoms, alkoxy of 1 to 6 carbon atoms, alkanoyloxy of 2 to 7 carbon atoms, halo or trifluoromethyl; and
  $R_6$ is hydrogen or halo;
or a pharmaceutically acceptable salt thereof.

Within this group of compounds there resides a preferred group of compounds which, in addition to their antidepressant activity, also possess anti-anxiety properties. The most preferred antidepressant-anti-anxiety compounds of this invention present the structural formula:

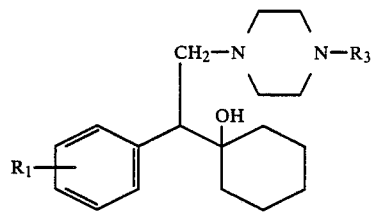

in which
  n is one of the integers 0, 1 or 2;
  o is one of the integers 0, 1 or 2;
  $R_1$ is hydrogen, alkoxy of 1 to 3 carbon atoms or hydroxy;
  $R_2$ is alkoxy of 1 to 3 carbon atoms or hydroxy and, when $R_1$ is hydrogen and n is zero, $R_2$ can be halo or trifluoromethyl;
  $R_1$ and $R_2$ aken together are 3,4-methylenedioxy; and
  $R_3$ is benzyl, chlorobenzyl, trifluoromethylbenzyl, alkoxybenzyl, chlorophenyl, trifluoromethylphenyl or alkoxyphenyl in which said alkoxy groups contain from 1 to 3 carbon atoms;
or a pharmaceutically acceptable salt thereof.

In addition, there resides within the group of compounds of this invention some purely antidepressant compounds of the formula:

in which
  $R_1$ is halo, trifluoromethyl, hydroxy or alkoxy of 1 to 6 carbon atoms; and
  $R_3$ is alkyl of 1 to 3 carbon atoms, preferably methyl, or a pharmaceutically acceptable salt thereof.

Substitution of the benzene ring, in all of these compounds, is preferably by hydroxy, methoxy, halo and trifluoromethyl groups. The halo groups include chloro, bromo, iodo and fluoro substituents. The pharmaceutically acceptable salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic and similar acids. For parenteral administration, the use of water soluble salts is preferred, while either the free base or the pharmaceutically acceptable salts are applicable for oral administration.

The compounds of this invention are prepared by conventional methods. In general, the compounds in which n is equal to zero are efficiently obtained by the following procedure:

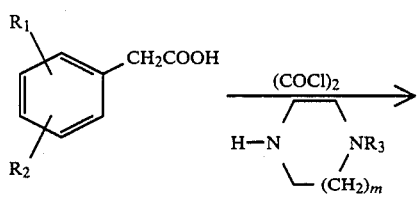

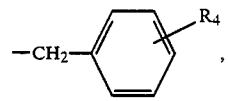

but it is to be understood that the other variables representing $R_3$ in the group of compounds of this invention are similarly applicable and their preparation is illustrated in the working examples:

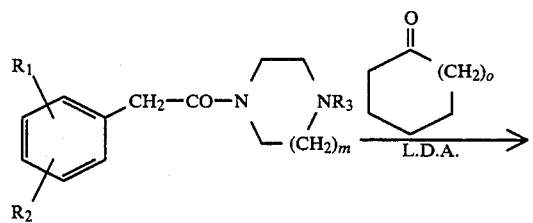

The amide produced from the appropriately substituted phenylacetic acid is treated with a cycloalkanone and a hydroxycycloalkyl intermediate is obtained. This is converted to the desired end product using a borane/THF reduction following the procedure of Brown et al., *J. Org. Chem.*, 38, 912 (1973). When $R_3$ is —CH$_2$—C$_6$H$_5$, it may be removed by catalytic hydrogenation and a different $R_3$ group may be reintroduced, tailored as desired.

The following procedure illustrates the tailoring of the $R_3$ substituent with

In the removal of an N-benzyl group by hydrogenation, $R_1$ and $R_2$ cannot be a halogen because hydrogenolysis of aromatic halogen occurs during removal of the benzyl substituent.

When n is one or two, a different preparative technique was employed as may be depicted by the following steps in which n has the value of one:

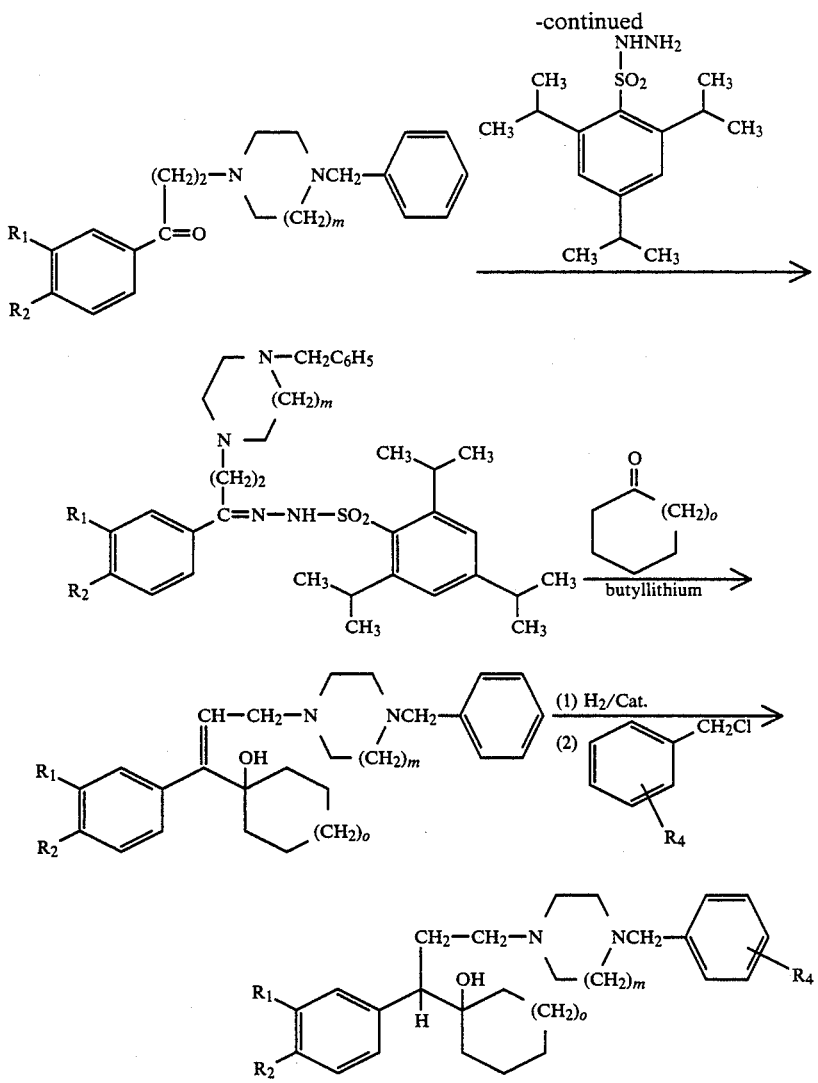

In this procedure, the piperazine propiophenone and piperazine butyrophenone intermediates may be obtained directly as follows:

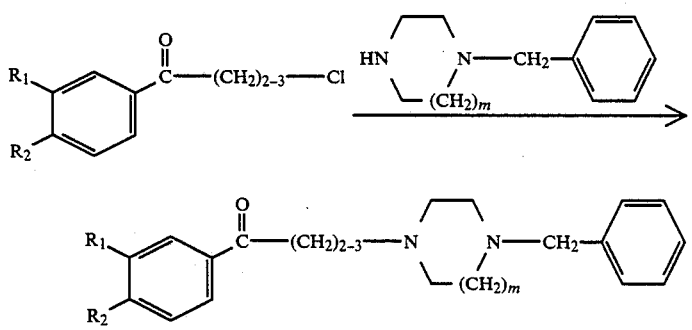

The reaction product, obtained from either process, is converted to the tris(1-methylethyl)benzenesulfonylhydrazone using the Bond modification of the Shapiro reaction [Chamberlain et al., *J. Org. Chem.*, 43, 147 (1978)]. The hydrazone yields a vinyl anion which condenses with a cycloalkanone to form the cycloalkanol. Catalytic hydrogenation debenzylates the piperazine moiety and gives a mixture of the saturated and unsaturated intermediate products. The desired, saturated end products of the reaction sequence are obtained by reintroduction of the $R_3$ group as follows:

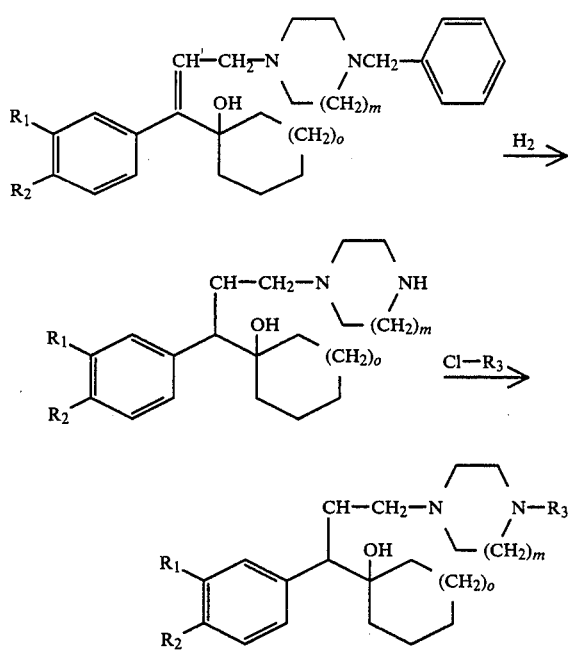

In this procedure, the $R_1$ and $R_2$ substituents are present as methoxy substituents in the 3- and/or 4-positions of the benzene ring for optimum product yields.

During the course of the synthesis of the end compounds of the invention by means of processes identified above, any hydroxy group may be in the free form or in the form of hydroxy protected by a removable protecting group. The protected form is recommended where the hydroxy group may otherwise undergo an undesired reaction. Examples of protecting groups for the hydroxy substituent are given in Protective Groups in Organic Chemistry edited by J. F. W. McOmie, Chapters 3 and 4 (pages 95-182) published by Plenum Press (1973), and Protective Groups in Organic Chemistry by T. W. Greene, Chapters 2 and 3 (pages 10 to 113) published by John Wiley and Sons (1981). The protecting group may be removed at a suitable later stage in the synthesis.

The final products contain an asymmetric center which, via conventional techniques of resolution, affords the individual optical isomers of the compounds.

In the production of the compounds of this invention, the preparation of certain key intermediates are best illustrated by the following detailed preparative schemes:

I n=1

1-[1-(3-Methoxyphenyl)-3-(piperazinyl)propyl]cyclohexanol (a)
1-(3-Methoxyphenyl)-3-[4-(phenylmethyl)-1-piperazinyl]-1-propanone A mixture of 3-methoxyacetophenone (53.8 g, 0.35 mole), paraformaldehyde (12.6 g), 1-benzylipiperazine dihydrochloride (106.2 g, 0.43 mole), ethanol (560 mL) and concentrated HCl (1.05 mL) was stirred and refluxed for 16 hours. The reaction mixture was cooled in ice and the product separated. The dihydrochloride was filtered using ice-cold ethanol, washed with diethyl ether and dried in a desiccator under vacuum. Yield 50.8 g, m.p. 256°-259° C.

Elemental Analysis for: $C_{21}H_{26}N_2O_2.2HCl$. Calculated: C, 61.31; H, 6.86; N, 6.81. Found: C, 61.25; H, 6.99; N, 6.89.

(b) 2,4,6-Tris-(1-methylethyl)benzenesulfonic acid [1-(3-methoxyphenyl)-3-[4-(phenylmethyl)-1-piperazinyl]propylidene]hydrazide To a suspension of 2,4,6-tris-(1-methylethyl) benzenesulfonylhydrazide (30 g, 0.01 mole) in a mixture of methanol (80 mL), diethyl ether (70 mL) and 5N isopropanolic HCl (30 mL) was added 1-(3-methoxyphenyl)-3-[4-(phenylmethyl)-1-propanone, dihydrochloride (42 g, 0.1 mole) and water (45 mL). The mixture was stirred at room temperature for 16 hours. The solid precipitate was filtered, washed with ethyl acetate and air dried. The free base was obtained as follows: the solid was partitioned between ethyl acetate and 4N NaOH solution (800 mL, 1:1 (v/v)). The phases were separated. The aqueous phase was extracted with ethyl acetate and the combined organic phase washed with brine, dried over magnesium sulfate and evaporated. The title compound, as a solid residue, was triturated with hexane and air dried, yield 42 g, m.p. 256°-259° C.

Elemental Analysis for: $C_{36}H_{50}N_4O_3S.\frac{1}{3}$ $H_2O$. Calculated: C, 69.20; H, 8.12; N, 8.97. Found: C, 69.30; H, 7.98; N, 8.85.

(c)
1-[1-(3-Methoxyphenyl)-3-[4-(phenylmethyl)-1-piperazinyl]-1-propenyl]cyclohexanol 2,4,6-Tris(1-methylethyl)benzenesulfonic acid [1-(3-methoxyphenyl)-3-[4-(phenylmethyl)-1-piperazinyl]-propylidene]hydrazide (42 g, 0.068 mole) was dissolved in dry dimethoxyethane (575 mL) under nitrogen with stirring. The solution was cooled to −78° C. and n-butyllithium (78 mL, 2.5M) was added dropwise. The mixture was allowed to warm to 0° C. and was stirred at this temperature for 15 minutes, during which time the reaction mixture became dark brown in color. The mixture was cooled to −50° C. and excess cyclohexanone (11.5 mL) added. The reaction mixture was stirred for 1.5 hours during which time the color dissipated as the reaction approached ambient temperature. The mixture was poured into a diethyl ether-N HCl mixture (400 mL, 1:1 v/v). The phases were separated. The aqueous phase was extracted with diethyl ether and the organic phase with N HCl. The combined aqueous (acidic) phase was basified with solid KOH and extracted twice with ethyl acetate. The extract was washed with brine, dried over magnesium sulfate and evaporated to an amorphous solid. Wt. 14 g. The product was dissolved in diethyl ether and the solution treated with excess 4N-isopropanolic HCl. The dihydrochloride of the title compound was obtained, m.p. 230°-232° C.

Elemental Analysis for: $C_{27}H_{36}N_2O_2.2HCl.H_2O$. Calculated: C, 63.39; H, 7.88; N, 5.48. Found: C, 63.35; H, 7.78; N, 5.81.

(c)
1-[1-(3-Methoxyphenyl)-3-(1-piperazinyl)propyl]cyclohexanol

A solution of 1-(3-Methoxyphenyl)-3-(1-piperazinyl)propyl]cyclohexanol

A solution of 1-[1-(3-methoxyphenyl)-3-[4-(phenylmethyl)-1-piperazinyl]-1-propenyl]cyclohexanol (3.09 g, 7.1 mmole) in ethanol (50 mL) containing sodium formate (0.5 g, 7.1 mmole) and formic acid (1.5 g, 30 mmole) was added to a suspension of 10% Pd/C (3.0 g) in ethanol (50 mL) and the mixturre refluxed for 2 hours under nitrogen. The catalyst was filtered and the filtrate evaporated. The residue was partitioned between 4N sodium hydroxide (200 mL) and ethyl acetate (200 mL). The layers were separated. The aqueous phase was extracted with ethyl acetate. The combined organic solution was washed with brine, dried over magnesium sulfate and evaporated to obtain the title compound as an oil.

Yield 1.9 g. Mass spectral analysis: Molecular weight by chemical ionization M+1 at 334.

II n=1

1-[1-(4-Methoxyphenyl)-3-(piperazinyl)propyl]cyclohexanol (a)

1-[1-(4-Methoxyphenyl)-3-[4-(phenylmethyl)-1-piperazinyl]-1-propenyl]cyclohexanol By replacing 1,4,6-tris(1-methylethyl)benzenesulfonic acid [1-(3-methoxyphenyl)-3-[4-phenylmethyl-1-piperazinyl]propylidene]hydrazide in I(c) with a molar equivalent amount of 2,4,6-tris(1-methylethyl)benzenesulfonic acid [1-(4-methoxyphenyl)-3-[4-phenylmethyl-1-piperazinyl]propylidene]hydrazide and following the procedure described therein, 1-[1-(4-methoxyphenyl)-3-[4-(phenylmethyl)-1-piperazinyl]-1-propenyl]cyclohexanol was obtained in 90% yield. The product was coverted to the dihydrochloride using 4N-isopropanolic HCl, m.p. 214°–216° C., yield 42%.

Elememental Analysis for: $C_{27}H_{30}N_2O_2 \cdot 2$ HCl. Calculated: C, 65.71; H, 7.76; N, 5.68. Found: C, 65.41; H, 7.39; N, 5.79.

(b)

1-[1-(4-Methoxyphenyl)-3-(1-piperazinyl)propyl]cyclohexanol

A solution of 1-[1-(4-methoxyphenyl)-3-[4-(phenylmethyl)-1-piperazinyl]-1-propenyl]cyclohexanol, dihydrochloride (14.6 g, 29.6 mmole) in ethanol (250 mL) was hydrogenated in a Parr apparatus over 10% Pd/C for 65 hours. The catalyst was filtered and the filtrate evaporated. The residue was partitioned between ethyl acetate (120 mL) and N sodium hydroxide (65 mL). The layers were separated. The aqueous phase was extracted with ethyl acetate. The combined organic solution was washed with brine, dried over magnesium sulfate and evaporated to obtain the title compound as an oil. Wt. 7.8 g. Mass spectral analysis: Molecular weight by C.I.M.S.: M+1 334.

III n=2

1-[1-(4-Methoxyphenyl)-4-[4-(phenylmethyl)-1-piperazinyl]-1-butenyl]cyclohexanol (a)

1-(4-Methoxyphenyl)-4-[4-phenylmethyl)-1-piperazinyl]-1-butanone

A mixture of γ-chloro-p-methoxybutyrophenone (45 g, 210 mole) 1-benzylpiperazine (35 mL, 200 mole) and anhydrous potassium carbonate (250 g) in methylisobutylketone (800 mL) was refluxed under nitrogen for 40 hours. The reaction mixture was cooled, poured into a beaker containing ice, then ethyl acetate was added. The layers were separated. The organic phase was washed with water, brine, dried over $K_2CO_3$ and evaporated to an oil. This residue was dissolved in diethyl ether (200 mL) and treated with excess 4N-isopropanolic HCl. The hydrochloride was obtained. Wt. 53 g. The product was purified as free base using column chromatography. It was then converted to the dihydrochloride of the title compound, m.p. 173°–175° C.

Elememental Analysis for: $C_{23}H_{28}N_2O_2 \cdot 2$ HCl $1\frac{1}{2}$ $H_2O$. Calculated: C, 58.4; H, 6.69; N, 6.19. Found: C, 58.48; H, 7.09; N, 6.05.

(b)

1-[1-(4-Methoxyphenyl)-4-[4-(phenylmethyl)-1-piperazinyl]-1-butenyl]cyclohexanol By replacing 2,4,6-tris-(1-methylethyl)benzenesulfonic acid [1-3-methoxyphenyl)-3-[4-(phenylmethyl)-1-piperazinyl]propylidene]hydrazide in I(c) with 2,4,6-tris-(1-methylethyl)benzenesulfonic acid [1-(4-methoxyphenyl)-4-[4-(phenylmethyl)-1-piperazinyl]butylidene]hydrazide and following the procedure described therein, the title compound was obtained. The product was dissolved in diethyl ether and treated with an isopropanolic solution of succinic acid (2 equivalents). The di-succinate was obtained in crystalline form, m.p. 146°–148° C.

Elemental Analysis for: $C_{28}H_{38}N_2O_2 \cdot 2$ $C_4H_6O_4$. Calculated: C, 64.46; H, 7.53; N, 4.17. Found: C, 64.11; H, 7.29; N, 4.30.

IV n=0

(a)

1-[(3-Methoxyphenyl)acetyl]-4-(phenylmethyl)piperazine

3-Methoxyphenylacetic acid (100 g, 600 mmole) was dissolved in methylene chloride (600 mL) and treated with oxalyl chloride (60 mL) and DMF (1 mL) at room temperature. The mixture was stirred for four hours until gas evolution ceased. The solvent was evaporated and the residue dried under vacuum to remove excess oxalyl chloride. The oil obtained was dissolved in methylene chloride (400 mL). Half of this solution (200 mL, approx. 300 mmole) was cooled in ice and treated with a solution of 1-benzylpiperazine (60 mL, 350 mmole) and triethylamine (30 mL) in methylene chloride (100 mL) dropwise. The mixture was stirred at room temperature for 16 hours. Sodium bicarbonate solution was added and the mixture stirred for 15 minutes. The layers were separated. The organic phase was washed with water, brine, dried over $K_2CO_3$ and evaporated to an oil. Wt. 90 g. A small portion was characterized as the hydrochloride, m.p. 229°–231° C.

Elemental Analysis for: $C_{20}H_{24}N_2O_2 \cdot HCl$. Calculated: C, 66.74; H, 7.02; N, 7.79. Found: C, 66.78; H, 6.91; N, 7.87.

(b)

1-(3-Chlorophenyl)-4-[(3-methoxyphenyl)acetyl]piperazine

By replacing 1-benzylpiperazine with a molar equivalent amount of 3-chlorophenylpiperazine in IV(a) and following the procedure described therein, the title compound was obtained as an oil. Mass spectral analysis: Molecular weight by C.I.M.S.: 344.5 (M+345, 347).

(c) 1-[(3-Methoxyphenyl)acetyl]-4-[3-(trifluoromethyl)phenyl]piperazine

By replacing 1-benzylpiperazine with a molar equivalent of 3-trifluoromethylphenylpiperazine in IV(a) and following the procedure described therein, the title compound was obtained as a crystalline solid, m.p. 99°–101° C.

Elemental Analysis for: $C_{20}H_{21}N_2O_2F_3$. Calculated: C, 63.48; H, 5.61; N, 7.04. Found: C, 63.40; H, 5.59; H, 7.47.

(d) 1-[(3-Chlorophenyl)acetyl]-4-(3-chlorophenyl)piperazine

By replacing 3-methoxyphenylacetic acid in IV(b) with a molar equivalent amount of 3-chlorophenylacetic acid, the title compound was obtained as an oil.

(e) 1-[(4-Fluorophenyl)acetyl]-4-(phenylmethyl)piperazine

By replacing 3-methoxyphenylacetic acid with a molar equivalent of 4-fluorophenylacetic acid in IV(a), the title compound was obtained as a crystalline solid, m.p. 99°–101° C.

Elemental Analysis for: $C_{19}H_{21}N_2OF$. Calculated: C, 73.04; H, 6.79; N, 9.06. Found: C, 72.83; H, 6.57; N, 9.06.

(f) 1-(Phenylmethyl)-4-[3-[(trifluoromethyl)phenyl]acetyl]piperazine

By replacing 3-methoxyphenylacetic acid in IV(a) with a molar equivalent amount of 3-trifluoromethylphenylacetic acid and following the procedure described therein, the title product was obtained as an oil.

(g) 1-[(3-Chlorophenyl)acetyl]-4-methyl piperazine

By replacing 1-benzylpiperazine in IV(d) with a molar equivalent amount of N-methyl piperazine and following the procedure described therein, the title compound was obtained as an oil.

(h) 1-[(4-Methoxyphenyl)acetyl]-4-methyl piperazine

By replacing 3-methoxyphenylacetic acid with 4-methoxyphenylacetic acid and 1-benzyl piperazine in IV(a) with a molar equivalent amount of N-methyl piperazine, the above intermediate was obtained as an oil.

(i) 1-Methyl-4-[3-(trifluoromethyl)acetyl]piperazine

By replacing 4-methoxyphenylacetic acid in IV(h) with a molar equivalent amount of 3-trifluoromethylphenylacetic acid, the intermediate was obtained as an oil.

(j) 1-[(3-Fluorophenyl)acetyl]-4-methyl piperazine

By replacing 4-methoxyphenylacetic acid in IV(h) with a molar equivalent amount of 3-fluorophenylacetic acid, the above intermediate was obtained as an oil.

The following examples illustrate, without limitation, the method employed in production of the products of this invention.

EXAMPLE 1

1-[1-(3-Methoxyphenyl)-3-[4-(phenylmethyl)-1-piperazinyl]propyl]cyclohexanol

Benzyl chloride (0.88 g, 6.8 mmole) was added to a solution of 1-[1-(3-methoxyphenyl)-3-(1-piperazinyl)propyl]cyclohexanol (1.8 g, 5.4 mmole) in DMF (50 mL) containing cesium carbonate (5.3 g, 1.6 mmole). The reaction mixture was stirred for one hour at room temperature. Triethylamine (0.23 mL) was added and the reaction mixture stirred for an additional 24 hours. The solvent was evaporated and the residue partitioned between water and chloroform (50:50 v/v). The aqueous solution was extracted with chloroform and the combined organic solution washed with brine, dried over magnesium sulfate and evaporated to an oil. Wt. 2.8 g. Column chromatography on silica gel with chloroform yielded 900 mg of pure product. This was dissolved in diethyl ether and treated with isopropanolic HCl affording the dihydrochloride salt, m.p. 249°–257° C.

Elemental Analysis for: $C_{27}H_{38}N_2O_2.2$ HCl.$\frac{3}{4}$ $H_2O$. Calculated: C, 63.71; H, 8.07; N, 5.50. Found: C, 64.09; H, 8.03; N, 5.50.

EXAMPLE 2

1-[1-(3-Methoxyphenyl)-3-[4-(2-pyrimidinyl)-1-piperazinyl]propyl]cyclohexanol

By replacing benzyl chloride in Example 1 with a molar equivalent amount of 2-chloropyrimidine, the title compound was obtained as a dihydrochloride, hemihydrate, m.p. 172°–174° C.

Elemental Analysis for: $C_{24}H_{34}N_4O_2.2$ HCl.$\frac{1}{2}$ $H_2O$. Calculated: C, 58.53; H, 7.57; N, 11.38. Found: C, 59.07; H, 7.74; N, 11.13.

EXAMPLE 3

1-[3-[4-(6-Chloro-2-pyrazinyl)-1-piperazinyl]-1-(3-methoxyphenyl)propyl]cyclohexanol By replacing benzyl chloride in Example 1 with a molar equivalent amount of 2,6-dichloropyrazine, the title compound was obtained as the hydrochloride, hydrate, m.p. 133°–135° C.

Elemental Analysis for: $C_{24}H_{33}N_4O_2C..HCl.H_2O$. Calculated: C, 57.71; H, 7.26; N, 11.22. Found: C, 58.22; H, 7.14; N, 10.74.

EXAMPLE 4

1-[3-[4-[(3-Chlorophenyl)methyl]-1-piperazinyl]-1-(3-methoxyphenyl)propyl]cyclohexanol By replacing benzyl chloride in Example 1 with 3-chlorobenzyl chloride and following the procedure described there, the title compound was obtained as the dihydrochloride, monohydrate, m.p. 241°–243° C.

Elemental Analysis for: $C_{27}H_{37}N_2O_2Cl.2$ $HCl.H_2O$. Calculated: C, 59.18; H, 7.17; N, 5.11. Found: C, 59.10; H, 7.69; N, 5.29.

EXAMPLE 5

1-[3-[4-[(4-Chlorophenyl)methyl]-1-piperazinyl]-1-(3-methoxyphenyl)propyl]cyclohexanol By replacing benzyl chloride in Example 1 with a molar equivalent amount of 4-chlorobenzyl chloride and following the procedure described therein, the title compound was obtained as the dihydrochloride hydrate, m.p. 253°–258° C.

Elemental Analysis for: $C_{27}H_{37}N_2OCl.2$ $HCl.H_2O$. Calculated: C, 59.18; H, 7.17; N, 5.11. Found: C, 59.58; H, 7.55; N, 5.23.

EXAMPLE 6

1-[1-(3-Methoxyphenyl)-3-[4-[(2-methoxyphenyl)methyl]-1-piperazinyl]propyl]cyclohexanol By replacing benzyl chloride in Example 1 with a molar equivalent amount of 2-methoxybenzyl chloride, the title compound was obtained as the dihydrochloride, hemihydrate, m.p. 226°–228° C.

Elemental Analysis for: $C_{28}H_{40}N_2O_3.2$ $HCl.\frac{1}{2}$ $H_2O$. Calculated: C, 62.91; H, 8.11; N, 5.24. Found: C, 63.23; H, 8.13; N, 5.30.

EXAMPLE 7

1-[3-[4-[(3-Fluorophenyl)methyl]-1-piperazinyl]-1-(3-methoxyphenyl)propyl]cyclohexanol By replacing benzyl chloride in Example 1 with a molar equivalent amount of 3-fluorobenzyl chloride, the title compound was obtained. The free base was dissolved in diethyl ether and treated with an isopropanolic solution of succinic acid (2 equivalents( yielding the di-succinate, hemihydrate, m.p. 131°–133° C.

Elemental Analysis for: $C_{27}H_{37}O_2N_2F.2(CH_2COOH)_2.\frac{1}{2}$ $H_2O$. Calculated: C, 61.30; H, 7.35; N, 4.08. Found: C, 61.41; H, 7.09; N, 4.02.

EXAMPLE 8

1-[1-(4-Methoxyphenyl)-3-[4-(phenylmethyl)-1-piperazinyl]propyl]cyclohexanol

Benzyl chloride (0.4 mL, 3.5 mmole) was added to a solution of 1-[1-(4-methoxyphenyl)-3-(1-piperazinyl)propyl]cyclohexanol (760 mg, 1.3 mmol) in DMF (25 mL) containing cesium carbonate (2.3 g, 7.1 mmole). The reaction mixture was stirred at room temperature for 2 hours. Triethylamine (0.9 mL, 6.4 mmol) was added and the reaction mixture stirred at room temperature an additional 20 hours. The solvent was evaporated. The residue was partitioned between water (150 mL) and methylene chloride (80 mL). The layers were separated. The aqueous phase was extracted twice with methylene chloride (80 mL) and the combined organic solution washed with water, brine, dried over magnesium sulfate and evaporated to an oil. Wt. 900 mg. This was dissolved in diethyl ether and treated with 2 equivalents of oxalic acid. The dioxalate, hemihydrate was isolated. Wt. 500 mg., m.p. 225°–227° C. Yield=36%.

Elemental Analysis for: $C_{27}H_{38}N_2O_2.2$ $C_2H_2O_4.\frac{1}{2}$ $H_2O$. Calculated: C, 60.87; H, 7.09; N, 4.58. Found: C, 61.24; H, 7.27; N, 4.29.

EXAMPLE 9

1-[3-[4-(6-Chloro-2-pyrazinyl)-1-piperazinyl]-1(4-methoxyphenyl)propyl]cyclohexanol By replacing benzyl chloride in Example 8 with a molar equivalent amount of 2,6-dichloropyrazine, the title compound was obtained as the oxalate, monohydrate, m.p. 204°–207° C.

Elemental Analysis for: $C_{24}H_{33}N_4O_2Cl.H_2O.C_2H_2O_4$. Calculated: C, 56.46; H, 6.74; N, 10.13. Found: C, 59.59; H, 6.48; N, 9.57.

EXAMPLE 10

1-[1-(4-Methoxyphenyl)-3-[4-[(3-methoxyphenyl)methyl]-1-piperazinyl propyl]cyclohexanol By replacing benzyl chloride in Example 8 with a molar equivalent amount of 3-methoxybenzyl chloride and following the procedures described therein, the title compound was obtained. The free base was dissolved in diethyl ether and treated with 4N isopropanolic HCl, yielding the dihydrochloride, hemihydrate, m.p. 198°–202° C.

Elemental Analysis for: $C_{28}H_{40}N_2O_3.2$ $HCl.\frac{1}{2}$ $H_2O$. Calculated: C, 62.91; H, 8.11; N, 5.24. Found: C, 63.01; H, 8.27; N, 5.25.

EXAMPLE 11

1-[1-(4-Methoxyphenyl)-3-[4-[[3-(trifluoromethyl)phenyl]methyl]-1-piperazinyl]propyl]cyclohexanol By replacing benzyl chloride in Example 8 with a molar equivalent amount of 3-trifluoromethylbenzyl chloride and following the procedure therein, the title compound was prepared as the dioxalate, monohydrate salt, m.p. 215°–219° C.

Elemental Analysis for: $C_{28}H_{37}N_2O_2F_3.2$ $C_2H_2O_4.H_2O$. Calculated: C, 55.80; H, 6.29; N, 4.06. Found: C, 55.23; H, 6.02; N, 4.00;

EXAMPLE 12

1-[3-[4-[(3-Chlorophenyl)methyl]-1-piperazinyl]-1-(4-methoxyphenyl)propyl]cyclohexanol By replacing benzyl chloride in Example 8 with a molar equivalent amount of 3-chlorobenzyl chloride and following the procedures described therein, the title compound was obtained as the dioxalate, hemihydrate, m.p. 223°–225° C.

Elemental Analysis for: $C_{27}H_{37}N_2O_2Cl.2$ $C_2H_2O_4.\frac{1}{2}$ $H_2O$. Calculated: C, 57.62; H, 6.55; N, 4.34. Found: C, 57.76; H, 6.38; N, 4.46.

EXAMPLE 13

1-[1-(4-Methoxyphenyl)-3-[4-(2-methoxyphenyl)methyl]-1-piperazinyl]propyl]cyclohexanol By replacing benzyl chloride in Example 8 with a molar equivalent of 2-methoxybenzyl chloride, the title compound was obtained as the dioxalate, m.p. 216°–218° C.

Elemental Analysis for: $C_{28}H_{40}N_2O_3.2$ $C_2H_2O_4$. Calculated: C, 60.74; H, 7.01; N, 4.43. Found: C, 60.80; H, 7.47; N, 3.99.

EXAMPLE 14

1-[1-(4-Methoxyphenyl)-3-[4-[[4-(trifuloromethyl)phenyl]methyl]-1-piperazinyl]propyl]cyclohexanol By replacing benzyl chloride in Example 8 with a molar equivalent amount of 4-trifluoromethylbenzyl bromide and following the procedures described therein, the title compound was obtained as the free base. The oil was dissolved in diethyl ether and treated with and isopropanolic solution of succinic acid (2 eqs.) and the di-succinate, hemihydrate was obtained, m.p. 148°–152° C.

Elemental Analysis for: $C_{28}H_{37}N_2O_2F_3.2$ $C_4H_6O_4.\frac{1}{2}$ $H_2O$. Calculated: C, 58.76; H, 6.85; N, 3.81. Found: C, 58.82; H, 6.69; N, 3.76.

EXAMPLE 15

1-[1-(3-Methoxyphenyl)-2-[4-(phenylmethyl)-1-piperazinyl]ethyl]cyclohexanol

Lithium di-isopropylamide (L.D.A.) was prepared by dissolving diisopropylamine (144 mL) in THF (200 mL) followed by the addition of 2.7 moles N-butyllithium 37 mL), The solution was cooled to, $-78°$ C., and a solution of 1-[(3-methoxyphenyl)acetyl]-4-(phenylmethyl)piperazine (32 g, 100 mmole) in THF (100 mL) added slowly. The reaction mixture was stirred at $-78°$ C. for 30 minutes. Excess cyclohexanone (2 equivalents was added and the mixture stirred at $-78°$ C. for 30 minutes. The reaction mixture was poured into saturated ammonium chloride solution (200 mL). The layers were separated. The aqueous layer was extracted with diethyl ether and the combined organic extract washed with brine, dried over $K_2CO_3$ and evaporated to an oil. The oil was dissolved in THF (100 mL) and added to an ice-cold solution of borane/THF complex (200 mL, 200 mmole). The mixture was refluxed for 2 hours and cooled again in an ice/acetone bath. 6N HCl (50 mL) was slowly added and the reaction mixture refluxed for 1 hour. The reaction mixture was cooled in ice/acetone and basified with solid KOH pellets. The layers were separated. The organic layer was washed with brine, dried over $K_2CO_3$ and evaporated to an oil, Wt. 24 g. The product was dissolved in diethyl ether and treated with 2 equivalents of 4N-isopropanolic HCl. The dihydrochloride was isolated, m.p. 233°–235° C.

Elemental Analysis for: $C_{25}H_{36}N_2O_2.2$ HCl. Calculated: C, 64.86; H, 7.95; N, 5.82. Found: C, 64.22; H, 8.04; N, 6.27.

EXAMPLE 16

1-[2-[4-(Phenylmethyl)]-1-piperazinyl]-1-[3-(trifluoromethyl)phenyl]ethyl]cyclohexanol By replacing 1-[(3-methoxyphenyl)acetyl]-4-phenylmethyl]piperazine in Example 15 with a molar equivalent amount of 1-[(3-trifluoromethyl)phenyl]acetyl]-4-(phenylmethyl)piperazine, the title compound was obtained as the dihydrochloride, monohydrate.

Elemental Analysis for: $C_{26}H_{33}N_2OF_3.2$ $HCl.H_2O$. Calculated: C, 58.09; H, 6.76; N, 5.21. Found: C, 58.23; H, 6.26; N, 5.16.

EXAMPLE 17

1-[1-(4-Fluorophenyl)-2-[4-(phenylmethyl)-1-piperazinyl]ethyl]cyclohexanol

By replacing 1-[(3-methoxyphenyl)acetyl]-4-phenylmethyl]piperazine in Example 15 with a molar equivalent amount of 1-[(4-fluorophenyl)acetyl]-4-(phenylmethyl)piperazine, the title compound was obtained as the dihydrochloride salt, hemihydrate.

Elemental Analysis for: $C_{25}H_{33}N_2OF.2$ $HCl.\frac{1}{2}$ $H_2O$. Calculated: C, 62.75; H, 7.24; N, 5.86. Found: C, 63.10; H, 7.39; N, 5.70.

EXAMPLE 18

1-[2-[3-(3-Chlorophenyl)-1-piperazinyl]-1-(3-methoxyphenyl)ethyl]cyclohexanol

By replacing 1-[(3-methoxyphenyl)acetyl]-4-(phenylmethyl)piperazine with a molar equivalent amount of 1-(3-chlorophenyl)-4-[(3-methoxyphenyl)acetyl]piperazine in Example 15, the title compound was obtained as a dihydrochloride, m.p. 178°–180° C.

Elemental Analysis for: $C_{25}H_{33}N_2O_2Cl.2$ HCl. Calculated: C, 59.81; H, 7.03; N, 5.60. Found: C, 60.62; H, 7.10; N, 6.17.

EXAMPLE 19

1-[1-(3-Chlorophenyl)-2-[4-(3-chlorophenyl)-1-piperazinyl]ethyl]cyclohexanol

Replacement of 1-[(3-methoxyphenyl)acetyl]-4-(phenylmethyl)piperazine in Example 15 with a molar equivalent of 1-[(3-chlorophenyl)acetyl]-4-(3-chlorophenyl)piperazine afforded the title compound as a dihydrochloride salt, m.p. 191°–193° C.

Elemental Analysis for: $C_{24}H_{30}N_2O.2HCl$. Calculated: C, 56.93; H, 5.97; N, 5.53. Found: C, 56.35; H, 6.23; N, 5.75.

EXAMPLE 20

1-[1-(3-Methoxyphenyl)-2-[4-[3-(trifluoromethyl)phenyl]-1-piperazinyl]ethyl]cyclohexanol By replacing 1-[(3-methoxyphenyl)acetyl]-4-(phenylmethyl)piperazine in Example 15 with a molar equivalent amount of 1-[(3-methoxyphenyl)acetyl]-4-[3-(trifluoromethyl)phenyl]piperazine and following the procedure described therein, the title compound was obtained as a citrate, hemihydrate, m.p. 150°–152° C.

Elemental Analysis for: $C_{26}H_{33}N_2O_2F_3.C_6H_8O_7.\frac{1}{2}$ $H_2O$. Calculated: C, 57.91; H, 6.39; N, 4.22. Found: C, 58.19; H, 6.33; N, 4.02.

EXAMPLE 21

1-[1-(3-Methoxyphenyl)-2-[4-[3-(trifluoromethyl)phenyl]-1-piperazinyl]ethyl]cyclopentanol By replacing cyclohexanone with a molar equivalent amount of cyclopentanone in Example 20, the title compound was obtained. The free base was converted to the maleate salt, m.p. 158°–160° C.

Elemental Analysis for: $C_{25}H_{31}N_2O_2F_3.C_4H_4O_4$. Calculated: C, 61.69; H, 6.28; N, 4.96. Found: C, 61.37; H, 6.11; N, 5.02.

EXAMPLE 22

1-[2-[4-[(3-Chlorophenyl)methyl]-1-piperazinyl]-1-(3-methoxyphenyl)ethyl]cyclohexanol To a suspension of 10% Pd/C (2.4 g) in ethanol (50 mL) was added a solution of 1-[1-(3-methoxyphenyl)-2-[4-(phenylmethyl)-1-piperazinyl]ethyl cyclohexanol (13.2 g, 32.2 mmole) in ethanol containing 4N isopropanolic HCl (18 mL). Ammonium formate (8.2 g, 129 mmole) was added and the mixture refluxed for 2 hours. The hot solution was filtered and the filtrate evaporated. The residue was partitioned between ethyl acetate and 4N sodium hydroxide (100:100 v.v). The layers were separated. The aqueous phase was extracted with ethyl acetate and the combined organic solution washed with brine, dried over $Na_2SO_4$ and evaporated yielding the secondary amine, 1-[1-(3-methoxyphenyl)-2-[1-piperazinyl]ethyl]cyclohexanol, 9.5 g. This secondary amine, 2.3 g, 7.2 mmole was dissolved in DMF (65 mL). Cesium carbonate (7.1 g, 21.8 mmole) and 3-chlorobenzyl chloride (1.5 g, 9 mmole) were added and the mixture stirred at room temperature for one hour. The reaction mixture was then treated with triethylamine (0.3 mL) and stirring continued for 24 hours. The solvent was evaporated and the residue partitioned between water and chloroform. The layers were separated. The aqueous solution was extracted with chloroform and the combined organic extract washed with brine, dried over Na₂SO₄ and evaporated (crude yield 4.7 g). Column chromatography on silica gel with chloroform yielded pure product (1.4 g). This was dissolved in diethyl ether and treated with an isopropanolic solution of fumaric acid. The fumarate, hemihydrate salt was isolated, m.p. 188°–191° C.

Elemental Analysis for: $C_{26}H_{35}N_2O_2Cl.2C_4H_4O_4.\frac{1}{2}H_2O$. Calculated: C, 59.69; H, 6.63; N, 4.09. Found: C, 60.03; H, 6.16; N, 4.04.

EXAMPLE 23

1-[2-[4-(6-Chloro-2-pyrazinyl)-1-piperazinyl]-1-(3-methoxyphenyl)ethyl]cyclohexanol By replacing 3-chlorobenzyl chloride with a molar equivalent amount of 2,6-dichloropyrazine in Example 22 and following the procedures described therein, the title compound was obtained. The free base was converted to the maleate salt, m.p. 157°–158° C.

Elemental Analysis for: $C_{23}H_{31}N_4O_2Cl.C_4H_4O_4$. Calculated: C, 59.28; H, 6.45; N, 10.24. Found: C, 59.29; H, 6.67; N, 10.22.

EXAMPLE 24

1-[1-(4-Methoxyphenyl)-3-[4-(2-pyrimidinyl)-1-piperazinyl propyl]cyclohexanol

By replacing benzyl chloride in Example 1 with a molar equivalent amount of 2-chloropyrimidine and following the procedure described therein, the title compound was obtained as the free base. This was then converted to the oxalate salt, m.p. 193°–196° C.

Elemental Analysis for: $C_{24}H_{34}N_4O_2.C_2H_2O_4$. Calculated: C, 62.38; H, 7.25; N, 11.19. Found: C, 62.04; H, 7.26; N, 10.75.

EXAMPLE 25

1-[1-(3-Fluorophenyl)-2-(4-methyl)-1-piperazinylethyl]-cyclohexanol

By replacing 1-[(3-methoxyphenyl)acetyl]-4-phenylmethylpiperazine in Example 15 with a molar equivalent amount of 1-[(3-fluorophenyl)acetyl]-4-methyl piperazine, the title compound was obtained as a dihydrochloride, m.p. 264°–266° C.

Elemental Analysis for: $C_{19}H_{29}N_2OF.2\ HCl$. Calculated: C, 58.01; H, 7.94; N, 7.12. Found: C, 57.79; H, 7.86, N, 6.96.

EXAMPLE 26

1-[1-(3-Chlorophenyl)-2-(4-methyl-1-piperazinyl)ethyl]-cyclohexanol

By replacing 1-(3-methoxyphenyl)acetyl-4-phenylmethylpiperazine in Example 15 with a molar equivalent amount of 1-(3-chlorophenyl)acetyl-4-methyl piperazine, the title compound was obtained as a dihydrochloride, m.p. 253°–255° C.

Elemental Analysis for: $C_{19}H_{29}N_2OCl.2HCl$. Calculated: C, 55.68; H, 7.62; N, 6.83. Found: C, 55.53; H, 7.30; N, 6.59.

EXAMPLE 27

1-[2-(4-Methyl-1-piperazinyl)-1-[3-(trifluoromethyl)-phenyl]ethyl]cyclohexanol

By replacing 1-(3-methoxyphenyl)acetyl-4-phenylmethylpiperazine in Example 15 with a molar equivalent amount of 4-methyl-1-8 (3-trifluoromethylphenyl)acetyl]piperazine, the title compound was obtained as the dihydrochloride, m.p. 245°–248° C.

Elemental Analysis for: $C_{20}H_{29}N_2OF_3.2\ HCl$. Calculated: C, 54.17; H, 7.04; N, 6.32. Found: C, 53.74; H, 6.86; N, 6.56.

EXAMPLE 28

1-[1-(4-Methoxyphenyl)-2-(4-methyl-1-piperazinyl)ethyl]cyclohexanol

By replacing 1-(3-methoxyphenyl)acetyl-4-phenylmethylpiperazine in Example 15 with a molar equivalent amount of 1-(4-methoxyphenyl)acetyl-4-methylpiperazine, the title compound was obtained as a dihydrochloride, m.p. 234°–236° C.

Elemental Analysis for: $C_{20}H_{32}N_2O_2.2HCl$. Calculated: C, 59.53; H, 8.57; N, 6.95. Found: C, 59.56; H, 8.27; N, 6.69.

EXAMPLE 29

1-[1-(3-Bromo-4-methoxyphenyl)-2-[4-(phenylmethyl)-1-piperazinyl]ethyl]cyclohexanol The title compound is obtained by first replacing 3-methoxyphenyl acetic acid in IV(a) with a molar equivalent amount of 3-bromo-4-methoxyphenyl acetic acid and using the amide obtained therein as a replacement for 1-(3-methoxyphenyl)acetyl-4-(phenylmethyl)-piperazine in Example 15.

EXAMPLE 30

1-[1-(4-Methoxyphenyl)-4-[4-(phenylmethyl)-1-piperazinyl]butyl]cyclohexanol

Following the procedure of Example 22, the intermediate produced in paragraph III(b), supra, is hydrogenated to obtain 1-[1-(4-methoxyphenyl)-4-(1-piperazinyl)butyl]cyclohexanol, which is rebenzylated routinely following the procedure indicated in the same example to give the title compound.

The antidepressant activity of the compounds of this invention was established by demonstrating their ability to inhibit synaptosomial uptake of norepinephrine (3H-NE) and/or serotonin ($^{14}$C-5-HT) following the test procedure of Wood et al., *J. Neurochem.*, 37 795 (1981). The pharmacology of the compounds of Examples 26 and 27 typifies selective antidepressant activity.

The additional anxiolytic property possessed by some of the compounds of this invention was indicated by demonstrating their strong affinity at $5-HT_{1A}$ receptor binding sites through inhibition of [$^3$H] 8-hydroxy-2-(di-n-propylamino)tetralin binding at 5-HT binding sites in rat hippocampal tissue, following the procedure of Hall et al., *J. Neurochem.*, 44 1685 (1985). Typical of these compounds are the products of Examples 1 and 5.

Furthermore, as may be seen from the pharmacological data presented infra, some of the compounds embraced by the compound genus of this invention demonstrate relatively high affinity for dopamine $D_2$ receptors, which is indicative of antipsychotic activity [Seeman, Pharmacol. Rev. 32, 230 (1981)]. Examples of these compounds are those demonstrating in excess of about 60% inhibition of $^3$H-haloperidol binding at $D_2$ recptors found in homogenized limbic brain tissue at μM concentration of the test compound as determined in a modification of the test procedure of Fields et al., Brain Res., 136, 578 (1977) and Yamamura et al., eds., Neurotramsitter Receptor Binding, Raven Press, N.Y. (1978) as discussed in U.S. Pat. No. 4,636,563. The actual percentage reduction of $^3$H-haloperidol binding is reported infra and the larger the number, the greater the potential for dopamine D$_2$ receptor binding and antipsychotic activity. The products of Examples 4 and 11 demonstrate typical D$_2$ binding potential for those compounds with that property aspect of a generally recognized antipsychotic profile.

The pharmacological test data obtained for a representative number of compounds of this invention in accordance with the standard experimental test procedures disclosed above appear in the following table:

| Compound | Receptor Binding Ki (nM) or % Inhibition at 1 µM | | Neuronal Uptake IC$_{50}$ (µM) or % Inhibition at 10 µM | |
|---|---|---|---|---|
| | 5HT$_{1A}$ | D2 | NE | 5HT |
| Example 1 | 10 nM | 209 nM | 2.03 µM | 0.39 µM |
| Example 2 | 78% | 59% | | |
| Example 3 | 122 nM | 41% | | |
| Example 4 | 66% | 90% | | |
| Example 5 | 97% | 51% | 100% | 100% |
| Example 6 | 93% | 91% | | |
| Example 7 | 93% | 89% | | |
| Example 8 | 99% | 55% | 0.61 µM | 67% |
| Example 9 | 57% | 15% | | |
| Example 10 | 99% | 73% | | |
| Example 11 | 100% | 100% | | |
| Example 12 | 100% | 95% | | |
| Example 13 | 93% | 77% | | |
| Example 14 | 63% | 25% | | |
| Example 15 | 91% | 90% | | |
| Exmnple 18 | 97% | 39% | 38% | 62% |
| Example 19 | 94% | 32% | | |
| Example 24 | | 11% | | |
| Example 26 | 0 | 26% | 0.18 µM | 33% |
| Example 27 | 5% | 0% | 86% | 0 |
| Buspirone | 10 nM (97%) | 84% (78 nM) | | |

In qualitatively evaluating the above data, high activity values in NE and 5-HT uptake correlate with antidepressant activity; high activity values for inhibition of 5-HT$_{1A}$ binding (about 90% to 100%) corrrelate (by analogy with buspirone) with anxiolytic activity; high affinity values for D$_2$ receptor binding (greater than 80%) correlate with antipsychotic activity.

From these data, the activity profile of the compounds of this invention are seen to be useful in the treatment of psychiatric disorders, in some instances, combining very desirable antidepressant-anxiolytic properties or demonstrating pure antidepressant activity.

Hence, the compounds of this invention are antidepressant, antipsychotic and anxiolytic agents useful in the treatment of depression and in alleviating anxiety. As such, they may be administered neat or with a pharmaceutical carrier to a patient in need thereof. The pharmaceutical carrier may be solid or liquid.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin,, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of a specific psychiatric disorder must be subjectively determined by the attending physician. The variables involved include the specific psychosis or state of depression or anxiety and the size, age and response pattern of the patient.

What is claimed is:

1. A compound of the formula:

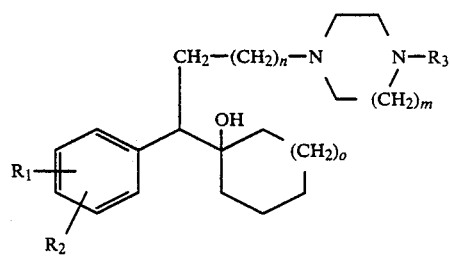

in which
m is one of the integers 1, 2 or 3;
n is one of the intergers 0, 1 or 2;
o is one of the integers 0, 1 or 2;

$R_1$ is alkoxy of 1 to 6 carbon atoms, hydroxyl, alkanoyloxy of 2 to 7 carbon atoms, alkyl of 1 to 6 carbon atoms, trifluoromethyl or halo;
$R_2$ is hydrogen, halo or alkoxy of 1 to 6 carbon atoms;
$R_1$ and $R_2$ taken together are 3,4-methylenedioxy;
$R_3$ is alkyl of 1 to 3 carbon atoms,

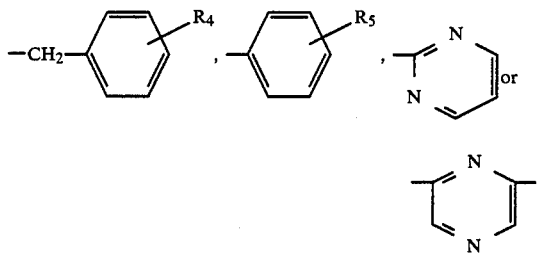

where $R_4$ and $R_5$ are, independently, hydrogen, hydroxyl, alkyl of 1 to 6 carbon atoms, alkoxy of 1 to 6 carbon atoms, alkanoyloxy of 2 to 7 carbon atoms, halo or trifluoromethyl; and $R_6$ is hydrogen or halo;
or a pharmaceutically acceptable salt thereof.

2. A compound of the formula:

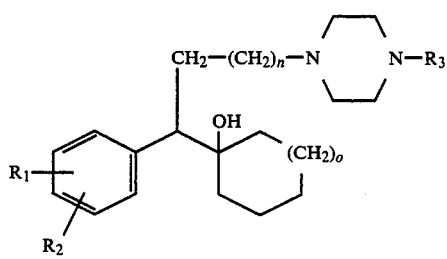

in which
n is one of the integers 0, 1 or 2;
o is one of the integers 0, 1 or 2;
$R_1$ is hydrogen, alkoxy of 1 to 3 carbon atoms or hydroxy;
$R_2$ is alkoxy of 1 to 3 carbon atoms or hydroxy and, when $R_1$ is hydrogen and n is zero, $R_2$ can be halo or trifluromethyl;
$R_1$ and $R_2$ taken together are 3,4-methylenedioxy; and
$R_3$ is benzyl, chlorobenzyl, trifluoromethylbenzyl, alkoxybenzyl, chlorophenyl, trifluoromethylphenyl or alkoxyphenyl in which said alkoxy groups contain 1 to 3 carbon atoms;
or a pharmaceutically acceptable salt thereof.

3. A compound of the formula:

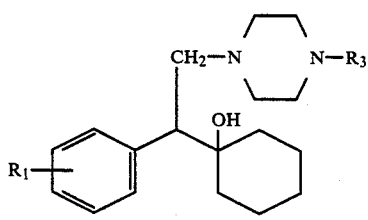

in which
$R_1$ is halo, trifluoromethyl, hydroxy or alkoxy of 1 to 6 carbon atoms; and
$R_3$ is alkyl of 1 to 3 carbon atoms;

or a pharmaceutically acceptable salt thereof.

4. A compound of claim 2 which is 1-[1-(3-methoxyphenyl)-3-[4-(phenylmethyl)-1-piperazinyl]propyl]cyclohexanol, or a pharmaceutically acceptable salt thereof.

5. A compound of claim 1 which is 1-[1-(3-methoxyphenyl)-3-methoxyphenyl)-3-[4-(2-pyrimidinyl)-1-piperazinyl]propyl]cyclohexanol, or a pharmaceutically acceptable salt thereof.

6. A compound of claim 1 which is 1-[3-[4-(6-chloro-2-pyrazinyl)-1-piperazinyl]-1-(3-methoxyphenyl)-propyl]cyclohexanol, or a pharmaceutically acceptable salt thereof.

7. A compound of claim 2 which is 1-[3-[4-[(3-chlorophenyl)methyl]-1-piperazinyl]-1-(3-methoxyphenyl)-propyl]cyclohexanol, or a pharmaceutically acceptable salt thereof.

8. A compound of claim 2 which is 1-[3-[4-[(4-chlorophenyl)methyl]-1-piperazinyl]-1-(3-methoxyphenyl)-propyl]cyclohexanol, or a pharmaceutically acceptable salt thereof.

9. A compound of claim 2 which is 1-[1-(3-methoxyphenyl)-3-[4-[(2-methoxyphenyl)methyl]-1-piperazinyl]propyl]cyclohexanol, or a pharmaceutically acceptable salt thereof.

10. A compound of claim 2 which is 1-[3-[4-[(3-fluorophenyl)methyl]-1-piperazinyl]-1-(3-methoxyphenyl)propyl]cyclohexanol, or a pharmaceutically acceptable salt thereof.

11. A compound of claim 2 which is 1-[1-(4-methoxyphenyl)-3-[4-(phenylmethyl)-1-piperazinyl]propyl]cyclohexanol, or a pharmaceutically acceptable salt thereof.

12. A compound of claim 1 which is 1-[3-[4-(6-chloro-2-pyrazinyl)-1-piperazinyl]-1-(4-methoxyphenyl)-propyl]cyclohexanol, or a pharmaceutically acceptable salt thereof.

13. A compound of claim 2 which is 1-[1-(4-methoxyphenyl)-3-[4-[(3-methoxyphenyl)methyl]-1-piperazinyl]propyl]cyclohexanol, or a pharmaceutically acceptable salt thereof.

14. A compound of claim 2 which is 1-[1-(4-methoxyphenyl)-3-[4-[[3-(trifluoromethyl)phenyl]methyl]-1-piperazinyl]propyl]cyclohexanol, or a pharmaceutically acceptable salt thereof.

15. A compound of claim 2 which is 1-[3-[4-[(3-chlorophenyl)methyl]-1-piperazinyl]-1-(4-methoxyphenyl)propyl]cyclohexanol, or a pharmaceutically acceptable salt thereof.

16. A compound of claim 2 which is 1-[1-(4-methoxyphenyl)-3-[4-(2-methoxyphenyl)methyl]-1-piperazinyl]-propyl]cyclohexanol, or a pharmaceutically acceptable salt thereof.

17. A compound of claim 2 which is 1-[1-(4-methoxyphenyl)-3-[4-[[4-(trifuloromethyl)phenyl]methyl]-1-piperazinyl]propyl]cyclohexanol, or a pharmaceutically acceptable salt thereof.

18. A compound of claim 2 which is 1-[1-(3-methoxyphenyl)-2-[4-(phenylmethyl)-1-piperazinyl]ethyl]cyclohexanol, or a pharmaceutically acceptable salt thereof.

19. A compound of claim 2 which is 1-[2-[4-(phenylmethyl)]-1-piperazinyl]-1-[3-(trifluoromethyl)phenyl]ethyl]cyclohexanol, or a pharmaceutically acceptable salt thereof.

20. A compound of claim 2 which is 1-[1-(4-fluorophenyl)-2-[4-(phenylmethyl)-1-piperazinyl]ethyl]cyclohexanol, or a pharmaceutically acceptable salt thereof.

21. A compound of claim 2 which is 1-[2-[4-(3-chlorophenyl)-1-piperazinyl]-1-(3-methoxyphenyl)ethyl]cyclohexanol, or a pharmaceutically acceptable salt thereof.

22. A compound of claim 2 which is 1-[1-(3-chlorophenyl)-2-[4-(3-chlorophenyl)-1-piperazinyl]ethyl]cyclohexanol, or a pharmaceutically acceptable salt thereof.

23. A compound of claim 2 which is 1-[1-(3-methoxyphenyl)-2-[4-[3-(trifluoromethyl)phenyl]-1-piperazinyl]ethyl]cyclohexanol, or a pharmaceutically acceptable salt thereof.

24. A compound of claim 2 which is 1-[1-(3-methoxyphenyl)-2-[4-[3-trifluoromethyl)phenyl]-1-piperazinyl]ethyl]cyclopentanol, or a pharmaceutically acceptable salt thereof.

25. A compound of claim 2 which is 1-[2-[4-[(3-chlorophenyl)methyl]-1-piperazinyl]-1-(3-methoxyphenyl)ethyl]cyclohexanol, or a pharmaceutically acceptable salt thereof.

26. A compound of claim 1 which is 1-[2-[4-(6-chloro-2-pyrazinyl)-1-piperazinyl]-1-(3-methoxyphenyl)ethyl]cyclohexanol, or a pharmaceutically acceptable salt thereof.

27. A compound of claim 1 which is 1-[1-[4-methoxyphenyl)-3-[4-(2-pyrimidinyl)-1-piperazinyl]propyl]cyclohexanol, or a pharmaceutically acceptable salt thereof.

28. A compound of claim 3 which is 1-[1-(3-fluorophenyl)-2-(4-methyl)-1-piperazinyl-ethyl]cyclohexanol, or a pharmaceutically acceptable salt thereof.

29. A compound of claim 3 which is 1-[1-(3-chlorophenyl)-2-(4-methyl-1-piperazinyl)ethyl]cyclohexanol, or a pharmaceutically acceptable salt thereof.

30. A compound of claim 3 which is 1-[2-(4-methyl-1-piperazinyl)-1-[3-(trifluoromethyl)phenyl]ethyl]cyclohexanol, or a pharmaceutically acceptable salt thereof.

31. A compound of claim 3 which is 1-[1-(4-methoxyphenyl)-2-(4-methyl-1-piperazinyl)ethyl]cyclohexanol, or a pharmaceutically acceptable salt thereof.

32. A compound of claim 2 which is 1-[1-(3-bromo-4-methoxyphenyl)-2-[4-(phenylmethyl)-1-piperazinyl]ethyl]cyclohexanol, or a pharmaceutically acceptable salt thereof.

33. A compound of claim 2 which is 1-[1-(4-methoxyphenyl)-4-[4-(phenylmethyl)-1-piperazinyl]butyl]cyclohexanol, or a pharmaceutically acceptable salt thereof.

34. A pharmaceutical composition comprising an anti-depressant amount of a compound of the formula:

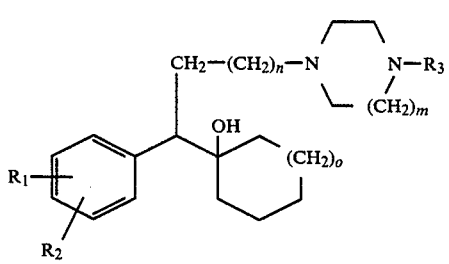

in which
m is one of the integers 1, 2 or 3;
n is one of the integers 0, 1 or 2;
o is one of the integers 0, 1 or 2;

$R_1$ is alkoxy of 1 to 6 carbon atoms, hydroxyl, alkanoyloxy of 2 to 7 carbon atoms, alkyl of 1 to 6 carbon atoms, trifluoromethyl or halo;
$R_2$ is hydrogen, halo or alkoxy of 1 to 6 carbon atoms;
$R_1$ and $R_2$ taken together are 3,4-methylenedioxy;
$R_3$ is alkyl of 1 to 3 carbon atoms;

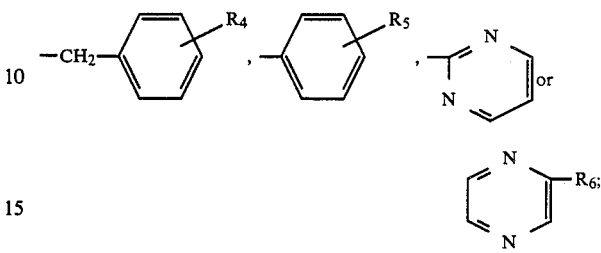

where $R_4$ and $R_5$ are, independently, hydrogen, hydroxyl, alkyl of 1 to 6 carbon atoms, alkoxy of 1 to 6 carbon atoms, alkanoyloxy of 2 to 7 carbon atoms, halo or trifluromethyl; and $R_6$ is hydrogen or halo;

or a pharmaceutically acceptable salt thereof, and a pharmaceutically acceptable carrier therefor.

35. A pharmaceutical composition comprising an anti-depressant/anxiolytic amount of a compound of the formula:

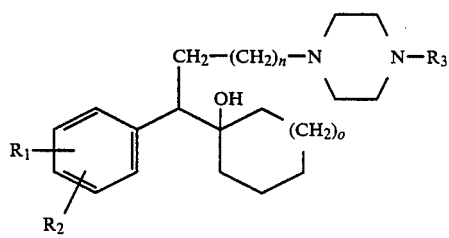

in which
n is one of the integers 0, 1 or 2;
o is one of the integers 0, 1 or 2;
$R_1$ is hydrogen, alkoxy of 1 to 3 carbon atoms or hydroxy;
$R_2$ is alkoxy or hydroxy and, when $R_1$ is hydrogen and n is zero, $R_2$ can be halo or trifluromethyl;
$R_1$ and $R_2$ taken together are 3,4-methylenedioxy; and
$R_3$ is benzyl, chlorobenzyl, trifluromethylbenzyl, chlorophenyl, trifluoromethylphenyl or alkoxyphenyl or a pharmaceutically acceptable salt thereof; and a pharmaceutically acceptable carrier therefor.

36. A pharmaceutical composition comprising an anti-depressant amount of a compound of the formula:

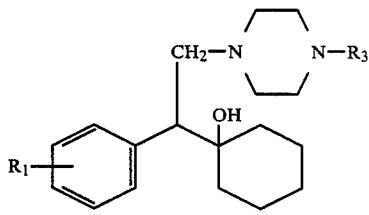

in which
$R_1$ is halo, trifluromethyl, hydroxy or alkoxy of 1 to 6 carbon atoms; and
$R_3$ is alkyl of 1 to 3 carbon atoms,
or a pharmaceutically acceptable salt thereof and a pharmaceutically acceptable carrier therefor.

* * * * *